US012697603B2

(12) United States Patent
Choi et al.

(10) Patent No.: US 12,697,603 B2
(45) Date of Patent: Aug. 4, 2026

(54) PRODUCTION OF POROUS ALPHA-ALUMINA SUPPORTS FROM BOEHMITIC DERIVED ALUMINAS

(71) Applicant: BASF SE, Ludwigshafen am Rhein (DE)

(72) Inventors: Sung Yeun Choi, Ludwigshafen am Rhein (DE); Andrey Karpov, Ludwigshafen am Rhein (DE); Christian Walsdorff, Ludwigshafen am Rhein (DE); Karl C. Kharas, Iselin, NJ (US)

(73) Assignee: BASF SE, Ludwigshafen am Rhein (DE)

( * ) Notice: Subject to any disclaimer, the term of this patent is extended or adjusted under 35 U.S.C. 154(b) by 786 days.

(21) Appl. No.: 18/011,543

(22) PCT Filed: Jun. 24, 2021

(86) PCT No.: PCT/EP2021/067398
§ 371 (c)(1),
(2) Date: Dec. 20, 2022

(87) PCT Pub. No.: WO2021/260140
PCT Pub. Date: Dec. 30, 2021

(65) Prior Publication Data
US 2023/0256415 A1      Aug. 17, 2023

(30) Foreign Application Priority Data
Jun. 26, 2020    (EP) .................................... 20182569

(51) Int. Cl.
B01J 21/04        (2006.01)
B01J 23/50        (2006.01)
(Continued)

(52) U.S. Cl.
CPC ............... B01J 21/04 (2013.01); B01J 23/50 (2013.01); B01J 35/635 (2024.01); B01J 35/638 (2024.01);
(Continued)

(58) Field of Classification Search
CPC . B01J 21/04; B01J 23/50; B01J 35/635; B01J 35/638; B01J 37/0009;
(Continued)

(56) References Cited

U.S. PATENT DOCUMENTS

| | | |
|---|---|---|
| 2,411,807 A | 11/1946 | Riesmeyer |
| 3,859,426 A | 1/1975 | Lambert |

(Continued)

FOREIGN PATENT DOCUMENTS

| | | |
|---|---|---|
| CN | 109499558 A | 3/2019 |
| DE | 2300512 A1 | 7/1973 |

(Continued)

OTHER PUBLICATIONS

Busca G. "The surface of transitional aluminas: A critical review," Catalysis Today vol. 226, May 1, 2014, pp. 2-13.

(Continued)

*Primary Examiner* — Cam N. Nguyen
(74) *Attorney, Agent, or Firm* — Faegre Drinker Biddle & Reath LLP

(57)        ABSTRACT

A porous alpha-alumina catalyst support is prepared by (i) preparing a precursor material comprising a boehmitic-derived alumina having a pore volume of at least 0.6 mL/g, wherein the boehmitic-derived alumina is obtained by thermal decomposition of a boehmitic starting material and the boehmitic starting material consists predominantly of block-shaped crystals, and optionally an inorganic bond material; (ii) forming the precursor material into shaped bodies; (iii) calcining the shaped bodies to obtain the porous alpha- (Continued)

alumina catalyst support. The support structure has a high overall pore volume, while keeping its surface area sufficiently large so as to provide optimal dispersion of catalytically active species, in particular metal species. The support is useful for a catalyst for producing ethylene oxide by gas-phase oxidation of ethylene.

12 Claims, 2 Drawing Sheets

(51) Int. Cl.

| | |
|---|---|
| *B01J 35/32* | (2024.01) |
| *B01J 35/55* | (2024.01) |
| *B01J 35/63* | (2024.01) |
| *B01J 35/70* | (2024.01) |
| *B01J 37/00* | (2006.01) |
| *B01J 37/02* | (2006.01) |
| *B01J 37/08* | (2006.01) |
| *C04B 35/111* | (2006.01) |
| *C04B 35/64* | (2006.01) |
| *C07D 301/10* | (2006.01) |

(52) U.S. Cl.
CPC ....... *B01J 37/0009* (2013.01); *B01J 37/0207* (2013.01); *B01J 37/088* (2013.01); *C07D 301/10* (2013.01); *B01J 35/32* (2024.01); *B01J 35/55* (2024.01); *B01J 35/70* (2024.01); *B01J 2235/15* (2024.01)

(58) Field of Classification Search
CPC ...... B01J 37/0207; B01J 37/088; B01J 35/32; B01J 35/55; B01J 35/70; B01J 2235/15; B01J 23/688; C07D 301/10; C04B 35/62695; C04B 35/63444; C04B 2235/3218; C04B 2235/602; C04B 2235/6021; C04B 2235/604; C04B 2235/661; C04B 2235/72; C04B 2235/725; C04B 2235/77; C04B 2235/788; C04B 2235/94; C04B 2235/945; C04B 35/111; Y02P 20/52
USPC ........................................................ 502/317
See application file for complete search history.

(56) References Cited

U.S. PATENT DOCUMENTS

| | | | | |
|---|---|---|---|---|
| 4,301,037 | A * | 11/1981 | Sanchez | B01J 35/60 |
| | | | | 423/628 |
| 4,356,312 | A | 10/1982 | Nielsen et al. | |
| 4,731,350 | A | 3/1988 | Boxhoorn et al. | |
| 4,732,918 | A | 3/1988 | Lohmueller | |
| 4,908,343 | A | 3/1990 | Bhasin | |
| 4,921,681 | A | 5/1990 | Ozero et al. | |
| 5,187,140 | A | 2/1993 | Thorsteinson et al. | |
| 5,504,052 | A | 4/1996 | Rizkalla et al. | |
| 5,504,053 | A | 4/1996 | Chou et al. | |
| 5,646,087 | A | 7/1997 | Rizkalla et al. | |
| 6,165,437 | A | 12/2000 | Mohri et al. | |
| 6,452,027 | B1 | 9/2002 | Billig et al. | |
| 7,553,795 | B2 | 6/2009 | Bortinger et al. | |
| 8,378,129 | B2 | 2/2013 | Bhise et al. | |
| 8,546,297 | B2 | 10/2013 | Rokicki et al. | |
| 8,685,883 | B2 * | 4/2014 | Bryden | B01J 23/66 |
| | | | | 502/355 |
| 9,101,906 | B2 * | 8/2015 | Bryden | B01J 35/633 |
| 9,233,942 | B2 * | 1/2016 | Lin | B01J 37/14 |
| 9,481,819 | B2 * | 11/2016 | Lee | C04B 35/1115 |
| 9,592,491 | B2 * | 3/2017 | Li | B01J 37/26 |
| 11,547,981 | B2 * | 1/2023 | Schwab | C04B 35/6316 |
| 2003/0191019 | A1 | 10/2003 | Rizkalla et al. | |
| 2006/0281631 | A1 | 12/2006 | Gerdes et al. | |
| 2008/0091038 | A1 | 4/2008 | Hirota et al. | |
| 2008/0193369 | A1 | 8/2008 | Barclay et al. | |
| 2008/0305333 | A1 | 12/2008 | Noweck et al. | |
| 2010/0056816 | A1 * | 3/2010 | Wallin | B01J 27/055 |
| | | | | 549/534 |
| 2011/0077152 | A1 | 3/2011 | Gerdes et al. | |
| 2012/0065055 | A1 * | 3/2012 | Jiang | B01J 37/08 |
| | | | | 502/216 |
| 2012/0108832 | A1 | 5/2012 | Chen et al. | |
| 2014/0187417 | A1 | 7/2014 | Pak | |
| 2021/0387958 | A1 | 12/2021 | Karpov et al. | |
| 2023/0234030 | A1 * | 7/2023 | Choi | B01J 35/651 |
| | | | | 549/536 |
| 2023/0256414 | A1 * | 8/2023 | Choi | B01J 35/653 |
| | | | | 502/347 |
| 2023/0256420 | A1 * | 8/2023 | Choi | C07D 301/10 |
| | | | | 502/347 |
| 2024/0293802 | A1 * | 9/2024 | Walsdorff | B01J 37/08 |

FOREIGN PATENT DOCUMENTS

| | | |
|---|---|---|
| DE | 2454972 A1 | 6/1975 |
| DE | 2521906 A1 | 12/1975 |
| DE | 3414717 A1 | 10/1985 |
| EP | 0014457 A2 | 8/1980 |
| EP | 0082609 A1 | 6/1983 |
| EP | 0085237 A1 | 8/1983 |
| EP | 0172565 A2 | 2/1986 |
| EP | 0266015 A1 | 5/1988 |
| EP | 0339748 A2 | 11/1989 |
| EP | 0357293 A1 | 3/1990 |
| EP | 0716884 A2 | 6/1996 |
| EP | 1115486 A1 | 7/2001 |
| EP | 1613428 A2 | 1/2006 |
| EP | 1893331 A1 | 3/2008 |
| EP | 1927398 A1 | 6/2008 |
| EP | 2617489 A1 | 7/2013 |
| EP | 3639923 A1 | 4/2020 |
| GB | 1512625 A | 6/1978 |
| WO | 00/15334 A1 | 3/2000 |
| WO | 03/72244 A1 | 9/2003 |
| WO | 03/72246 A2 | 9/2003 |
| WO | 03/86624 A1 | 10/2003 |
| WO | 2004/089537 A2 | 10/2004 |
| WO | 2004/094055 A2 | 11/2004 |
| WO | 2006/102189 A1 | 9/2006 |
| WO | 2006/133183 A2 | 12/2006 |
| WO | 2007/000664 A1 | 1/2007 |
| WO | 2008/054564 A1 | 5/2008 |
| WO | 2009/029419 A1 | 3/2009 |
| WO | 2010/000720 A2 | 1/2010 |
| WO | 2012/140614 A1 | 10/2012 |
| WO | 2014/105770 A1 | 7/2014 |
| WO | 2015/095508 A1 | 6/2015 |
| WO | 2019/039930 A1 | 2/2019 |
| WO | 2019/072597 A1 | 4/2019 |
| WO | 2019/154863 A1 | 8/2019 |
| WO | 2019/219892 A1 | 11/2019 |

OTHER PUBLICATIONS

Guzman-Castillo et al., "Effect of Boehmite Crystallite Size and Steaming on Alumina Properties," The Journal of Physical Chemistry B, vol. 105, No. 11, pp. 2099-2116.

Souza Santos et al., "Hydrothermal synthesis of well-crystallised boehmite crystals of various shapes," Materials Research, vol. 12, No. 4, 2009, pp. 437-445.

International Search Report and Written Opinion received for PCT Patent Application No. PCT/EP2021/067398, mailed on Oct. 1, 2021, 8 pages.

* cited by examiner

PRODUCTION OF POROUS ALPHA-ALUMINA SUPPORTS FROM BOEHMITIC DERIVED ALUMINAS

CROSS-REFERENCE TO RELATED APPLICATIONS

This application is a National stage application (under 35 U.S.C. § 371) of PCT/EP2021/067398, filed Jun. 24, 2021, which claims benefit of European Application No. 20182569.2, filed Jun. 26, 2020, both of which are incorporated herein by reference in their entirety.

The present invention relates to a process for producing a porous alpha-alumina catalyst support, a catalyst for producing ethylene oxide by gas-phase oxidation of ethylene comprising silver deposited on a porous alumina catalyst support, a process for preparing the catalyst, and a process for producing ethylene oxide by gas-phase oxidation of ethylene.

Alumina ($Al_2O_3$) is ubiquitous in supports and/or catalysts for many heterogeneous catalytic processes. Some of these catalytic processes occur under conditions of high temperature, high pressure and/or high water-vapor pressure. It is well known that alumina has a number of crystalline phases such as alpha-alumina (often denoted as $\alpha$-alumina or $\alpha$-$Al_2O_3$), gamma-alumina (often denoted as $\gamma$-alumina or $\gamma$-$Al_2O_3$) as well as a number of alumina polymorphs. Alpha-alumina is the most stable at high temperatures, but has the lowest surface area.

Gamma-alumina has a very high surface area. This is generally believed to be because the alumina molecules are in a crystalline structure that is not very densely packed. Gamma-alumina constitutes a part of the series known as activated aluminas or transition aluminas, so-called because it is one of a series of aluminas that can undergo transition to different polymorphs. Unfortunately, when gamma-alumina is heated to high temperatures, the structure of the atoms collapses such that the surface area decreases substantially. The most dense crystalline form of alumina is alpha-alumina.

Depending on the choice of starting material, transition aluminas and alpha-alumina obtained therefrom exhibit different morphologies, impacting properties such as the pore size, pore size distribution and surface area. The morphological properties, which are heavily dependent on the crystal shapes of the starting material, also impact the properties of alpha-alumina supports obtained from transition aluminas and/or alpha-alumina. This is described, e.g., by Guzmán-Castillo et al., J. Phys. Chem. B 105 (2001), 2099-2106.

Busca, Catalysis Today, 226 (2014), 2-13, describes that aluminas derived from a variety of pseudoboehmites have differing pore volumes and pore size distributions, despite the pseudoboehmites having similar surface areas (160–200 $m^2$/g). Different types of alumina crystal shapes are described, e.g., in de Souza Santos et al., Materials Research, 12 (2009), 4, 437-445, and include platelets, fibrous shapes and rod-like shapes.

Ethylene oxide is produced in large volumes and is primarily used as an intermediate in the production of several industrial chemicals. In the industrial oxidation of ethylene to ethylene oxide, heterogeneous catalysts comprising silver deposited on a porous support are typically used. To carry out the heterogeneously catalyzed gas-phase oxidation, a mixture of an oxygen-comprising gas, such as air or pure oxygen, and ethylene is generally passed through a plurality of tubes which are arranged in a reactor in which a packing of shaped catalyst bodies is present.

Catalyst performance is typically characterized by selectivity, activity, longevity of catalyst activity, and mechanical stability. Selectivity is the molar fraction of the converted olefin yielding the desired olefin oxide. Even small improvements in selectivity and the maintenance of selectivity over longer time yield huge dividends in terms of process efficiency.

For the internal surfaces of a porous supported catalyst to be utilized effectively, the feed gases must diffuse through the pores to reach the internal surfaces, and the reaction products must diffuse away from those surfaces and out of the catalyst body. In a process for producing ethylene oxide by gas-phase oxidation of ethylene, e.g., it appears that while ethylene usually passes into and out of the pores easily, the diffusion of the bulkier ethylene oxide takes significantly longer. Under the thus prolonged exposure, the ethylene oxide may undergo undesired consecutive reactions induced by the catalyst, such as complete combustion to carbon dioxide, which reduces the overall selectivity of the process.

Hence, the catalytic performance is influenced by the catalyst's pore structure, which is essentially determined by the pore structure of the catalyst support. The term "pore structure" is understood to relate to the arrangement of void spaces within the support matrix, including sizes, size distribution, shapes and interconnectivity of pores. It can be characterized by various methods such as mercury porosimetry, nitrogen sorption or computer tomography. H. Giesche, "Mercury Porosimetry: A General (Practical) Overview, Part. Part. Syst. Charact. 23 (2006), 9-19, provides helpful insights with regard to mercury porosimetry.

EP 2 617 489 A1 describes a catalyst carrier wherein at least 80% of the pore volume is contained in pores with diameters in the range of from 0.1 to 10 μm, and at least 80% of the pore volume in the pores with diameters in the range of from 0.1 to 10 μm is contained in pores with diameters in the range of from 0.3 to 10 μm.

WO 03/072244 A1 and WO 03/072246 A1 each describe a catalyst carrier wherein at least 70% of the pore volume is contained in pores with diameters of from 0.2 to 10 μm and pores with diameters between 0.2 and 10 μm provide a volume of at least 0.27 mL/g of the carrier.

WO 2006/133183 A2 describes a carrier having a pore size distribution wherein at least 80% of the total pore volume is contained in pores with diameters in the range of from 0.1 to 10 μm, and at least 80% of the pore volume contained in pores with diameters in the range of from 0.1 to 10 μm is contained in pores with diameters in the range of from 0.3 to 10 μm. The carrier may exhibit a non-platelet morphology.

EP 1 927 398 A1 describes a catalyst carrier having a pore size distribution with at least two maxima in the range of 0.01 to 100 μm, with at least one of these maxima being in the range of 0.01-1.0 μm.

EP 3 639 923 A1 describes a shaped catalyst body with a multimodal pore size distribution having a maximum in the range of 0.1 to 3.0 μm and a maximum in the range of 8.0 to 100 μm, wherein at least 40% of the total pore volume of the shaped catalyst body stems from pores with a diameter in the range of 0.1 to 3.0 μm.

WO 2008/054564 A1 describes a method for producing shaped porous bodies comprising alpha-alumina platelets. US 2006/0281631 A1 describes the preparation of a carrier comprising non-platelet alumina. U.S. Pat. No. 6,165,437 A describes the preparation of alpha-alumina powders with specific morphologies by calcination of transition alumina powder in a chlorine-containing atmosphere. WO 2006/133183 A2 describes carriers exhibiting non-platelet morphology, wherein "non-platelet morphology" refers to the substantial absence of structures having flat surfaces. The structures having a substantially flat surface are said to have typically an aspect ratio of at most 4:1, the aspect ratio being the ratio of the largest dimension to the smallest dimension of the structure.

There remains a significant need to enhance the performance of a supported catalyst by optimizing the alumina-based support structure and for a process for producing an optimized porous alpha-alumina catalyst support. The support structure should have a high overall pore volume, thus allowing for impregnation with a high amount of silver, while keeping its surface area sufficiently large so as to provide optimal dispersion of catalytically active species, in particular metal species. Moreover, a high pore connectivity is desired so as to allow for a high rate of intra-support diffusion.

The pore structure is determined by factors including size, size distribution and shape of the grains composing the matrix of the support. It has now been found that boehmitic-derived aluminas obtained by thermal decomposition of a boehmitic starting material consisting predominantly of block-shaped crystals are useful starting materials for the production of alpha-alumina catalyst supports with beneficial pore structure.

The invention relates to a process for producing a porous alpha-alumina catalyst support, comprising i) preparing a precursor material comprising a boehmitic-derived alumina having a pore volume of at least 0.6 mL/g and optionally an inorganic bond material, wherein the boehmitic-derived alumina is obtained by thermal decomposition of a boehmitic starting material and the boehmitic starting material consists predominantly of block-shaped crystals;

ii) forming the precursor material into shaped bodies; and iii) calcining the shaped bodies to obtain the porous alpha-alumina support.

In the obtained porous alpha-alumina catalyst support, the majority of the total pore volume is contained in pores with a diameter in the range of 0.1 to 1 μm, as shown in the examples discussed below.

Without wishing to be bound by theory, it is believed that pores with a diameter in the range of 0.1 to 1 μm provide a particularly suitable environment for catalytic conversion after application of a catalytic species, e.g., via impregnation. The pores are small enough to provide a large surface area, while being large enough for allowing quick diffusion of starting materials and obtained products, thus allowing for high activity and selectivity of catalysts based on such a catalyst support. Pores with a larger diameter are believed to not contribute significantly to the total surface area, thus providing less efficient reaction spaces. Pores with a diameter smaller than 0.1 μm are believed to hinder diffusion of the obtained products, which prolongs exposure of the products to the catalytic species and induces consecutive reactions, thus lowering the selectivity.

The term "boehmitic-derived alumina" is understood to relate to an alumina obtained by thermal decomposition of a boehmitic starting material, in particular boehmite or pseudoboehmite, most preferably boehmite. The boehmitic-derived alumina preferably comprises alpha-alumina, a transition alumina, or mixtures thereof, in particular a transition alumina, such as a gamma-, delta-, theta-alumina phase, in particular a phase selected from gamma-alumina and/or delta-alumina.

According to the invention, the boehmitic-derived alumina is obtained by thermal decomposition of a boehmitic starting material consisting predominantly of block-shaped crystals. Block-shaped crystals, as opposed to rod-shaped or platelet-shaped crystals, have similar dimensions in all three crystal directions. Block-shaped crystal may be described by their aspect ratio. Preferably, the block-shaped crystals have an aspect ratio of at most 3.0, preferably at most 2.5, wherein the aspect ratio is defined as the ratio of the largest crystal dimension to the smallest crystal dimension. "Crystal dimensions" are the dimensions along the three axes of the unit cell. The crystal dimensions may be determined via X-ray diffraction analysis and simulation of diffraction patterns from an ensemble of particles with a given structure, size, and shape, as explained in more detail in the examples that follow.

It is understood that a crystalline bulk material consists of a plurality of individual crystals which may have slightly different habitus. According to the invention, the boehmitic starting material consists predominantly of block-shaped crystals, which means that the boehmitic starting material consists of at least 50 wt.-% of block-shaped crystals, relative to the total weight of crystals constituting the boehmitic starting material. In a preferred embodiment, the boehmitic starting material consists of at least 60 wt.-% of block-shaped crystals, relative to the total weight of boehmitic starting material, more preferably at least 70 wt.-%, most preferably at least 80 wt.-%, relative to the total weight of crystals constituting the boehmitic starting material. Typically, the boehmitic starting material consists of crystals with a size less than about 100 nanometers, mostly 1 to 50 nm.

It is believed that the crystal shapes of the boehmitic starting material are essentially retained during conversion to transition alumina and finally alpha-alumina by heat treatment. This means that the morphological properties of the boehmitic starting material directly impact properties such as pore size, pore size distribution and surface area of the boehmitic-derived alumina and, accordingly, the porous alpha-alumina catalyst support derived therefrom.

The precursor material preferably comprises, based on inorganic solids content, at least 50 wt.-% of the boehmitic-derived alumina, preferably a transition alumina. Preferably, the precursor material comprises, based on inorganic solids content, at least 60 wt.-%, more preferably at least 70 wt.-% of the boehmitic-derived alumina, such as at least 80 wt.-% or at least 90 wt.-%, in particular 95 to 100 wt.-%.

The boehmitic-derived alumina is typically in the form of a powder. Boehmitic-derived aluminas are commercially available. They may be obtained on a large scale by thermal decomposition of a boehmitic starting material, most often boehmite.

By progressively heating the boehmitic starting material, lattice rearrangements are affected. For example, boehmite can be converted to gamma-alumina at about 450° C., gamma-alumina can be converted to delta-alumina at about 750° C., and delta-alumina can be converted to theta-alumina at about 1,000° C. When heating at above 1,000° C., transition aluminas are converted to alpha-alumina.

Block-shaped boehmite is commercially available as well. Generally, aluminum hydroxide is prepared by the "Bayer" method, which comprises dissolving kaolin in sodium hydroxide under high pressure and high temperature, leaching aluminum oxide into the solution, and producing aluminum hydroxide by hydrolysis of the leached solution. Gibbsite which is the primary product of the Bayer method can be converted into boehmite by several processes. However, the aluminum hydroxide prepared by the Bayer method contains a considerable amount of impurities.

Another typical method for preparing alumina having high purity, the so-called Ziegler process and variants thereof as described in Busca, Catalysis Today, 226 (2014), 2-13, comprises hydrolysis of aluminum alkoxide. Amorphous aluminum hydroxide is prepared by the hydrolysis of aluminum alkoxide, and then boehmite is prepared by crystallization. Several variables, including temperature, pH, or crystallization conditions from near-equilibrium growth conditions to kinetically controlled condition, may be modified during the crystallization of the particulate material to effect the desired morphology. Modifying crystal growth processes using crystallization modifiers is a well established approach. The habit modification may be attributed to the preferential adsorption of the modifier to the fastest growing crystal face of the crystal, which inhibits the crystal growth along the corresponding direction.

US 2008/0193369A discloses a method wherein a modifier such as lanthanum oxide or lanthanum hydroxide is added to an aqueous boehmite slurry. US 2008/305333 discloses a method for providing boehmitic aluminas having unusual morphologies. The boehmitic aluminas is prepared by hydrothermal aging of oxygen compounds of aluminum, optionally in the presence of nitrogen bases or oxides or oxide hydrates of zirconium, titanium, lanthanum, and/or boron.

Prior to heat treatment, the boehmitic starting materials may be washed, e.g., with demineralized water, so as to reduce impurities and allow for obtaining a high purity boehmitic-derived alumina. For example, crystalline boehmite obtained from gibbsite by a hydrothermal process according to Chen et al., J. Solid State Chem., 265 (2018), 237 to 243, is preferably washed prior to heat treatment.

Boehmitic-derived aluminas used in the present invention preferably have a total content of alkali metals, e.g., sodium and potassium, of at most 1500 ppm, more preferably at most 600 ppm and most preferably 10 to 200 ppm. Various washing methods are known that allow for the reduction of the alkali metal content of the boehmitic-derived alumina and/or the catalyst support obtained therefrom. Washing can include washing with a base, an acid, water or other liquids.

U.S. Pat. No. 2,411,807 A describes that the sodium oxide content in alumina precipitates may be reduced by washing with a solution containing hydrofluoric acid and another acid. WO 03/086624 A1 describes carrier pretreatment with an aqueous lithium salt solution so as to remove sodium ions from the surface of a carrier. U.S. Pat. No. 3,859,426 A describes the purification of refractory oxides such as alumina and zirconia by repetitive rinsing with hot deionized water. WO 2019/039930 describes a purification method of alumina in which metal impurities were removed by extraction with an alcohol.

The boehmitic-derived alumina has a pore volume of at least 0.6 mL/g, as determined by nitrogen sorption. Nitrogen sorption measurements may be performed using a Micrometrics ASAP 2420. Nitrogen porosity is determined according to DIN 66134 herein, unless stated otherwise. Preferably, the boehmitic-derived alumina has a pore volume of 0.6 to 2.0 mL/g or 0.65 to 2.0 mL/g, more preferably 0.7 to 1.8 mL/g, most preferably 0.8 to 1.6 mL/g, as determined by nitrogen sorption.

The boehmitic-derived alumina preferably has a median pore diameter of at least of 15 nm as determined by nitrogen sorption. The term "median pore diameter" is used herein to indicate the pore diameter above which half of the total pore volume exists. Thus, the median pore diameter differentiates between two sets of pores of the same combined pore volume, with each set representing 50% of the total pore volume. The pore diameters of one set of pores are above the median pore diameter, and the pore diameters of the other set of pores are below the median pore diameter. Preferably, the boehmitic-derived alumina has a pore diameter of 15 to 500 nm, more preferably 20 to 450 nm, most preferably 20 to 300 nm, such as 20 to 200 nm, as determined by nitrogen sorption.

The boehmitic-derived alumina preferably has a loose bulk density of at most 600 g/L. The term "loose bulk density" is understood to be the "freely settled" or "poured" density. The "loose bulk density" thus differs from the "tapped density", where a defined mechanical tapping sequence is applied and a higher density is typically obtained. The loose bulk density may be determined by pouring the boehmitic-derived alumina into a graduated cylinder, suitably via a funnel, taking care not to move or vibrate the graduated cylinder. The volume and weight of the alumina are determined. The loose bulk density is determined by dividing the weight in grams by the volume in liters.

A low loose bulk density may be indicative of a high porosity and a high surface area. Preferably, the boehmitic-derived alumina has a loose bulk density in the range of 50 to 600 g/L, more preferably in the range of 100 to 550 g/L, most preferably 150 to 500 g/L, in particular 200 to 450 g/L.

The boehmitic-derived alumina typically has a BET surface area in the range of 20 to 500 $m^2/g$. The BET method is a standard, well-known method and widely used method in surface science for the measurements of surface areas of solids by physical adsorption of gas molecules. The BET surface is determined according to DIN ISO 9277 herein, unless stated otherwise. The terms "BET surface area" and "surface area" are used equivalently herein, unless noted otherwise.

The BET surface area of the boehmitic-derived alumina may vary over a relatively large range and may be adjusted by varying the conditions of the thermal dehydration of the boehmitic starting material by which the boehmitic-derived alumina may be obtained. Preferably, the boehmitic-derived alumina has a BET surface area in the range of 20 to 200 $m^2/g$, more preferably 50 to 150 $m^2/g$.

Suitable boehmitic-derived aluminas are commercially available. In some instances, such commercially available transition aluminas are classified as "medium porosity aluminas" or, in particular, "high porosity aluminas". Suitable transition aluminas include products of the Puralox® TH and Puralox® TM series, both from Sasol.

The boehmitic-derived alumina may be used in its commercially available ("unmilled") form. Unmilled boehmitic-derived alumina powder typically has a $D_{50}$ particle diameter of 10 to 100 μm, preferably 20 to 50 μm. In addition, boehmitic-derived transition alumina may be used which has been subjected to grinding to break down the particles to a desired size. Suitably, the boehmitic-derived alumina may be milled in the presence of a liquid, and is preferably milled in the form of a suspension. Alternatively, grinding may be effected by dry ball-milling or by jet-milling. Milled boehmitic-derived alumina powder typically has a $D_{50}$ particle diameter of 0.5 to 8 μm, preferably 1 to 5 μm. The particle size of boehmitic-derived alumina may be measured by laser diffraction particle size analyzers, such as a Malvern Mastersizer using water as a dispersing medium. The method includes dispersing the particles by ultrasonic treatment, thus breaking up secondary particles into primary particles. This sonication treatment is continued until no further change in the $D_{50}$ value is observed, e.g., after sonication for 3 min. It is understood that the particles of boehmitic-derived alumina comprise microcrystallites of alumina less than one micron in size, which are agglomerated together where they contact one another.

In a preferred embodiment, the boehmitic-derived alumina comprises at least 50 wt.-%, preferably 60 to 90 wt.-% of a transition alumina having an average particle size of 10 to 100 µm, preferably 20 to 50 µm, based on the total weight of boehmitic-derived alumina. Optionally, the boehmitic-derived alumina may comprise a transition alumina having an average particle size of 0.5 to 8 µm, preferably 1 to 5 µm, such as at most 50 wt.-%, preferably 10 to 40 wt.-%, based on the total weight of boehmitic-derived alumina.

The precursor material may optionally comprise an inorganic bond material. Suitable inorganic bond materials are understood to be any of the inorganic species conventionally used in the art, e.g., aluminum compounds such as alumina hydrates, silicon-containing species such as silica or silicates, including clays such as kaolinite, or metal hydroxides, metal carbonates, metal nitrates, metal acetates or metal oxides such as zirconia, titania, or alkali metal oxides.

Inorganic bond materials are permanent bond materials, which contribute to the adequate bonding of alumina particles and enhance the mechanical stability of the shaped alpha-alumina bodies. The precursor material may comprise inorganic bond materials in amounts of 0.0 to 30.0 wt.-%, preferably 1 to 30 wt.-%, more preferably 1 to 25 wt.-%, most preferably 1 to 20 wt.-%, such as 3 to 18 wt.-%, based on the inorganic solids content of the precursor material.

Preferably, the inorganic bond material comprises an alumina hydrate. The term "alumina hydrate" is understood to relate to hydrated aluminum compounds, in particular hydrated aluminum hydroxides and hydrated aluminum oxy-hydroxides. A discussion of the nomenclature of aluminas may be found in K. Wefers and C. Misra, "Oxides and Hydroxides of Aluminum", Alcoa Laboratories, 1987. Suitable hydrated aluminum compounds include naturally occurring and synthetic compounds, such as aluminum trihydroxides like gibbsite, bayerite and nordstrandite, or aluminum oxy-monohydroxides like boehmite, pseudoboehmite and diaspore.

Preferably, the alumina hydrate comprises boehmite and/or pseudoboehmite. In a preferred embodiment, the total amount of boehmite and pseudoboehmite constitutes at least 80 wt.-%, more preferably at least 90 wt.-% and most preferably at least 95 wt.-%, such as 95 to 100 wt.-%, of the alumina hydrate. In an especially preferred embodiment, the amount of boehmite constitutes at least 80 wt.-%, more preferably at least 90 wt.-% and most preferably at least 95 wt.-%, such as 95 to 100 wt.-%, of the alumina hydrate.

Suitable alumina hydrates are commercially available and include products of the Pural® series from Sasol, preferably products of the Pural® TH and Pural® TM series, and products of the Versal® series from UOP.

Without wishing to be bound by theory, it is believed that the presence of alumina hydrate increases the mechanical stability of the support. In particular, it is believed that nano-sized, highly dispersible alumina hydrates suitable for colloidal applications, such as boehmites of the Disperal® or Dispal® series from Sasol exhibit high binding forces and can enhance the mechanical stability of the support especially efficiently. In general, using such nano-sized, highly dispersible alumina hydrates to improve mechanical stability may allow for relatively lower BET-surface areas at given calcination conditions.

Alumina hydrate may be partially or fully replaced by suitable alternative aluminum compounds while essentially retaining the mechanical stability of the support. Such suitable alternative aluminum compounds include aluminum alkoxides like aluminum ethoxide and aluminum isopropoxide, aluminum nitrate, aluminum acetate and aluminum acetylacetonate.

Preferably, the inorganic bond material comprises at least 80 wt.-%, more preferably at least 90 wt.-%, most preferably at least 95 wt.-% of alumina hydrate, relative to the total weight of inorganic bond material. Preferably, the precursor material comprises, based on inorganic solids content, 1 to 30 wt.-% of the alumina hydrate, more preferably 1 to 25 wt.-%, most preferably 1 to 20 wt.-%, such as 3 to 18 wt.-%. In a preferred embodiment, the precursor material does not comprise an inorganic bond material besides alumina hydrate.

The precursor material optionally comprises a liquid. The presence, type and amount of the liquid may be chosen in accordance with the desired handling properties of the precursor material. For example, the presence of the liquid may be desirable to obtain a malleable precursor material.

The liquid is typically selected from water, in particular de-ionized water, and/or an aqueous solution comprising soluble and/or dispersible compounds selected from salts, such as ammonium acetate and ammonium carbonate; acids, such as formic acid, nitric acid, acetic acid and citric acid; bases, such as ammonia, triethylamine and methylamine; surfactants such as triethanolamine, poloxamers, fatty acid esters, and alkyl polyglucosides; submicron-sized particles, including metal oxides such as silica, titania and zirconia; clays; and/or polymer particles such as polystyrene and polyacrylates. The liquid is preferably water, most preferably de-ionized water. Typical amounts of the liquid vary in the range of from 10 to 60 wt.-%, based on the inorganic solids content of the precursor material.

The precursor material may comprise further components, such as a burnout material. Suitable burnout materials include thermally decomposable biomaterials such as acacia, sawdust, and flours, in particular ground nut shell flours, such as flours of pecan shells, cashew shells, walnut shells or filbert shells;

powdered carbonaceous compounds such as coke, or carbon powders;

milled or unmilled carbon fibers tableting aids such as graphite or magnesium stearate;

lubricants, such as petroleum jelly, mineral oil, or grease;

organic polymers such as polysaccharides, such as starch, gums, cellulose and cellulose derivatives, including substituted celluloses such as methyl cellulose, ethyl cellulose, and carboxy ethyl cellulose, and cellulose ethers;

polyvinyl lactam polymers, such as polyvinylpyrrolidones, or vinylpyrrolidone copolymers such as vinylpyrrolidone-vinyl acetate copolymers;

polyolefins, like polyethylene and polypropylene;

aromatic hydrocarbon polymers, like polystyrene;

polycarbonates, such as poly(propylene carbonate);

polyalkylene glycols, such as polyethylene glycol;

lignins;

alcohols, in particular polyols such as glycol or glycerol;

fatty acid derivatives, such as esters of fatty acids, in particular esters of saturated fatty acids, such as stearate esters like methyl and ethyl stearate;

malleable organic solids such as waxes like paraffin wax, cetyl palmitate, and resins like epoxy resin and polyurethane resin; and combinations thereof.

Burnout materials, which sometimes are also referred to as "organic bond materials" or "temporary bond materials", may be used to maintain the porous structure of the precursor material during the "green" phase, i.e. the unfired phase, in which the mixture may be formed into shaped bodies. In general, burnout materials are essentially completely removed during calcination of the shaped bodies.

The precursor material may comprise the burnout material in amounts of 1.0 to 60 wt.-%, preferably 3 to 50 wt.-%, based on the total weight of the precursor material.

Some of the above-mentioned burnout materials, such as ground nut shell flours, constitute pore-forming materials. Such pore-forming materials may be used to improve the rate of intra-support diffusion by allowing for additional and/or wider pores in the support. The additional pore volume of wider pores can also advantageously allow for a more efficient impregnation of the support during the production of a catalyst.

Advantageously, burnout materials exhibit a low ash content. The term "ash content" is understood to relate to the incombustible component remaining after combustion of the burnout materials in air at high temperature, i.e. after calcining of the shaped bodies. The ash content is preferably below 0.1 wt.-%, relative to the weight of burnout materials.

Moreover, burnout materials preferably do not form significant amounts of volatile further combustible components, such as carbon monoxide or combustible organic compounds, upon calcining of the shaped bodies, i.e. upon thermal decomposition or combustion. An excess of volatile organic components may induce an explosive atmosphere.

The precursor material is typically obtained by dry-mixing its components, and then optionally adding the liquid. The precursor material may be formed into shaped bodies via extrusion, tableting, granulation, casting, molding, or micro-extrusion, in particular via extrusion or tableting.

The size and shape of the shaped bodies and thus of the catalyst is selected to allow a suitable packing of the catalysts obtained from the shaped bodies in a reactor tube. The catalysts obtained from the shaped bodies suitable for the catalysts of the invention are preferably used in reactor tubes with a length from 6 to 14 m and an inner diameter from 20 mm to 50 mm. In general, the support is comprised of individual bodies having a maximum extension in the range of 3 to 20 mm, such as 4 to 15 mm, in particular 5 to 12 mm. The maximum extension is understood to mean the longest straight line between two points on the outer circumference of the support.

The shape of the shaped bodies is not especially limited, and may be in any technically feasible form, depending, e.g., on the forming process. For example, the support may be a solid extrudate or a hollow extrudate, such as a hollow cylinder. In another embodiment, the support may be characterized by a multilobe structure. A multilobe structure is meant to denote a cylinder structure which has a plurality of void spaces, e.g., grooves or furrows, running in the cylinder periphery along the cylinder height. Generally, the void spaces are arranged essentially equidistantly around the circumference of the cylinder.

Preferably, the support is in the shape of a solid extrudate, such as pellets or cylinders, or a hollow extrudate, such as a hollow cylinder. In a preferred embodiment, the shaped bodies are formed by extrusion, e.g., micro-extrusion. In this case, the precursor material suitably comprises a liquid, in particular water, so as to form a malleable precursor material.

In a preferred embodiment, extrusion comprises charging at least one solid component into a mixing device before the liquid is added. Preferably, a mix-muller (H-roller) or a horizontal mixer such as a Ploughshare® mixer (from Gebrüder Lödige Maschinenbau) is used for mixing. The forming of an extrudable paste of the precursor material can be monitored and controlled based on data reflecting power consumption of the mixing device.

The precursor material is typically extruded through a die. The cross-section of the die opening is adapted according to the desired geometry of the shaped body.

The extrusion die may comprise a matrix and mandrels, wherein the matrix essentially determines the circumferential shape of the shaped bodies and the mandrels essentially determine the form, size and position of passageways, if present. Suitable extrusion dies are described in, e.g., WO 2019/219892 A1.

The geometry of the shape of the shaped bodies is defined by the ideal geometry of the extrusion apparatus through which the precursor material is extruded. Generally, the geometry of the shape of the extrudate differs slightly from the ideal geometry of the extrusion apparatus, while essentially having the geometric properties described above. Absolute sizes of the shape are in general slightly lower than the sizes of the extrudate, due to high temperatures required to form alpha alumina and shrinkage upon cooling of the extrudate. The extent of the shrinkage depends on the temperatures applied during calcination and the components of the shaped bodies. Therefore, the size of the extrusion dies should be routinely adjusted in a way to account for the extrudate shrinkage during the subsequent calcination.

When the shaped body comprises multiple passageways, the axes of the passageways typically run parallel. However, the shaped bodies may be slightly bent or twisted along their z axis (height). The shape of the cross-section of the passageways may be slightly different from the envisioned perfect geometrical shapes described above. When a large amount of shaped bodies is obtained, single passageways of a small number of the shaped catalyst bodies may be closed. Usually the face sides of the shaped catalyst bodies in the xy plane are more or less uneven, rather than smooth, due to the production process. The height of the shaped bodies (length of the shaped bodies in the z direction) is usually not exactly the same for all of the shaped bodies, but rather constitutes a distribution with an average height as its arithmetic mean.

The extrudate is preferably cut into the desired length while still wet. Preferably, the extrudate is cut at an angle essentially perpendicular to its circumferential surface. In order to reduce undesirable deviations from the ideal geometry of the extrusion apparatus, the extrudate may alternatively be cut at a slanted angle of up to 30°, such as 10° or 20°, with regard to the angle perpendicular to the circumferential surface of the extrudate.

Aberrations from the ideal geometry as incurred in the extrusion process and/or the further processing of the extrudate, e.g. a cutting step, may generally also be present in the porous alpha-alumina catalyst support of the invention obtained in the process of the invention without essentially lessening the favorable effects of its pore structure. The skilled person understands that perfect geometrical forms are fundamentally unobtainable due to the imprecision which is inherent to all production processes to some degree.

In order to facilitate forming of the shaped bodies by extrusion, preferable burnout materials of the precursor material include processing aids such as petroleum jelly and mineral oil, grease, and/or polyalkylene glycols such as polyethylene glycol. Processing aids may be used to increase the malleability of the precursor material. The precursor material may comprise the processing aid in amounts 1.0 to 10 wt.-%, preferably 3 to 8 wt.-%, based on the inorganic solids content of the precursor material.

In another embodiment, the precursor material is formed into shaped bodies using a micro-extrusion process such as the one described in WO 2019/072597 A1.

In another embodiment, the precursor material is formed into shaped bodies via tableting. In this case, the precursor material typically does not comprise a liquid. Tableting is a process of press agglomeration. A powdered or previously agglomerated bulk material is introduced into a pressing tool having a die between two punches and compacted by uniaxial compression and shaped to give a solid compact. This operation is divided into four parts: metered introduction, compaction (elastic deformation), plastic deformation and ejection. Tableting is carried out, for example, on rotary presses or eccentric presses.

If desired, the upper punch and/or lower punch may comprise projecting pins to form internal passageways. It is also possible to provide the pressing punches with a plurality of movable pins, so that a punch can, for example, be made up of five part punches ("ring punch" having four "holes" and four pins).

The pressing force during tableting affects compaction of the bulk material. In practice, it has been found to be useful to set the lateral compressive strength of the porous alpha-alumina catalyst support in a targeted manner by selection of the appropriate pressing force and to check this by random sampling. For the purposes of the present invention, the lateral compressive strength is the force which fractures the porous alpha-alumina catalyst support located between two flat parallel plates, with the two flat parallel end faces of the catalyst support being at right angles to the flat parallel plates.

For tableting, it is often preferably to make use of tableting aids such as graphite or magnesium stearate. To improve tableting properties, a pre-granulation and/or sieving step may be used. For pre-granulation, a roll compactor, such as a Chilsonator® from Fitzpatrick, may be used. Further information regarding tableting, in particular with regard to pre-granulation, sieving, lubricants and tools, may be found in WO 2010/000720 A2.

Prior to calcining, the shaped bodies may be dried, in particular when the precursor material comprises a liquid. Suitably, drying is performed at temperatures in the range of 20 to 400° C., in particular 30 to 300° C., such as 70 to 150° C. Drying is typically performed over a period of up to 100 h, preferably 0.5 h to 30 h, more preferably 1 h to 16 h.

Drying may be performed in any atmosphere, such as in an oxygen-containing atmosphere like air, in nitrogen, or in helium, or in mixtures thereof, preferably in air. Drying is usually carried out in an oven. The type of oven is not especially limited. For example, stationary circulating air ovens, revolving cylindrical ovens or conveyor ovens may be used. Heat may be applied directly and/or indirectly.

Preferably, flue gas (vent gas) from a combustion process having a suitable temperature is used in the drying step. The flue gas may be used in diluted or non-diluted form to provide direct heating and to remove evaporated moisture and other components liberated from the shaped bodies. The flue gas is typically passed through an oven as described above. In another preferred embodiment, off-gas from a calcination process step is used for direct heating.

Drying and calcination may be carried out sequentially in separate apparatuses and may be carried out in a batch-wise or continuous process. Intermittent cooling may be applied. In another embodiment, drying and calcination are carried out in the same apparatus. In a batch process, a time-resolved temperature ramp (program) may be applied. In a continuous process, a space-resolved temperature-ramp (program) may be applied, e.g., when the shaped bodies are continuously moved through areas (zones) of different temperatures.

Preferably, measures of heat-integration as known in the art are applied in order to improve energy efficiency. For example, relatively hotter off-gas from one process step or stage can be used to heat the feed gas, apparatus or shaped bodies in another process step or stage by direct (admixing) or indirect (heat-exchanger) means. Likewise, heat integration may also be applied to cool relatively hotter off-gas streams prior to further treatment or discharge.

The shaped bodies are calcined to obtain the porous alpha-alumina catalyst support. Thus, the calcination temperature and duration are sufficient to convert at least part of the transition alumina to alpha-alumina, meaning that at least part of the metastable alumina phases of the transition alumina is converted to alpha-alumina.

The obtained porous alpha-alumina catalyst support typically comprises a high proportion of alpha-alumina, for example at least 80 wt.-%, preferably at least 90 wt.-%, more preferably at least 95 wt.-%, most preferably at least 97.5 wt.-%, based on the total weight of the support. The amount of the alpha-alumina can for example be determined via X-ray diffraction analysis.

Typically, calcining is performed at a temperature of at least 1300° C., such as at least 1400° C., more preferably at least 1450° C., most preferably at least 1500° C. Preferably, calcining is performed at an absolute pressure in the range of 0.5 bar to 35 bar, in particular in the range of 0.9 to 1.1 bar, such as at atmospheric pressure (approximately 1013 mbar). Typical total heating times range from 0.5 to 100 h, preferably from 2 to 20 h.

Calcination is usually carried out in a furnace. The type of furnace is not especially limited. For example, furnaces such as stationary circulating air furnaces, revolving cylindrical furnaces or conveyor furnaces, or kilns such as rotary kilns or tunnel kilns, in particular roller hearth kilns, may be used.

Calcination may be performed in any atmosphere, such as in an oxygen-containing atmosphere like air, in nitrogen, or in helium, or in mixtures thereof. Preferably, in particular when the formed bodies contain a burnout material, calcination is at least in part or entirely carried out in an oxidizing atmosphere, such as in an oxygen-containing atmosphere like air.

As described above, burnout materials preferably do not form significant amounts of volatile further combustible components, such as carbon monoxide or combustible organic compounds, upon calcining of the shaped bodies. An explosive atmosphere may further be avoided by limiting the oxygen concentration in the atmosphere during calcination, e.g., to an oxygen concentration below the limiting oxygen concentration (LOC) with respect to the further combustible components. The LOC, also known as minimum oxygen concentration (MOC), is the limiting concentration of oxygen below which combustion is not possible.

Suitably, lean air or a gaseous recycle stream with limited oxygen content may be used along with a stream for oxygen make-up, which also compensates for gaseous purge streams. In an alternative approach, an explosive atmosphere can be avoided by limiting the rate of formation of further combustible components. The rate of formation of further combustible components may be limited by heating to the calcination temperature via a slow temperature ramp, or by heating in a step-wise manner. When heating in a step-wise manner, the temperature is suitably held for several hours at the approximate combustion temperature, then heating to temperatures of 1000° C. In a continuous calcination process, the feed rate of the shaped bodies to the calcination device, e.g., the furnace, may also be controlled so as to limit the rate of formation of further combustible components.

Depending on the nature of burnout materials and gaseous components, a waste-gas treatment may be applied in order to purify any off-gas obtained during calcination. Preferably, an acidic or alkaline scrubber, a flare or catalytic combustion, a DeNOx treatment or combinations thereof may be used for off-gas treatment.

Preferably, heating takes place in a step-wise manner. In step-wise heating, the shaped bodies may be placed on a high purity and inert refractory saggar which is moved through a furnace with multiple heating zones, e.g., 2 to 8 or 2 to 5 heating zones. The inert refractory saggar may be made of alpha-alumina or corundum, in particular alpha-alumina.

The porous alpha-alumina catalyst support obtained by the process of the invention typically has a BET surface in the range of 0.5 to 5.0 $m^2/g$. Preferably, the porous alpha-alumina catalyst support has a BET surface area in the range of 0.5 to 4.5 $m^2/g$, more preferably 1.0 to 4.5 $m^2/g$, most preferably 1.0 to 4.0 $m^2/g$.

The porous alpha-alumina catalyst support typically has a total pore volume of at least 0.2 mL/g, as determined by mercury porosimetry. Mercury porosimetry may be performed using a Micrometrics AutoPore IV 9500 mercury porosimeter (140 degrees contact angle, 485 dynes/cm Hg surface tension, 60,000 psia max head pressure). The mercury porosity is determined according to DIN 66133 herein, unless stated otherwise.

The porous alpha-alumina catalyst support obtained by the process of the invention typically has a pore volume contained in pores with a diameter in the range of 0.1 to 1 $\mu m$ of at least 40% of the total pore volume, as determined by mercury porosimetry. Preferably, the porous alpha-alumina catalyst support has a pore volume contained in pores with a diameter in the range of 0.1 to 1 $\mu m$ of at least 50% of the total pore volume, more preferably at least 55% of the total pore volume, most preferably at least 60% of the total pore volume, such as at least 65% or at least 70% of the total pore volume. Typically, the porous alpha-alumina catalyst support obtained by the process of the invention has a pore volume contained in pores with a diameter in the range of 0.1 to 1 $\mu m$ of preferably 40 to 99%, more preferably 45 to 99% most preferably 50 to 97% of the total pore volume.

The porous alpha-alumina catalyst support typically has a ratio $r_{pv}$ of the pore volume contained in pores with a diameter in the range of more than 1 to 10 $\mu m$ to the pore volume contained in pores with a diameter in the range of 0.1 to 1 $\mu m$ of at most 0.50. Preferably, the ratio of $r_{pv}$ is in the range of 0.0 to 0.45, more preferably 0.0 to 0.40 or 0.0 to 0.35.

The porous alpha-alumina support generally comprises at least 80 wt.-%, preferably at least 90 wt.-%, more preferably at least 95 wt.-%, most preferably at least 97.5 wt.-%, of alpha-alumina based on the total weight of the support.

In one embodiment, the porous alpha-alumina catalyst support comprises at least 80 wt.-% of alpha-alumina, the support having a BET surface area in the range of 0.5 to 5.0 $m^2/g$;

a total pore volume of at least 0.2 m/g, as determined by mercury porosimetry; and a pore volume contained in pores with a diameter in the range of 0.1 to 1 $\mu m$ of at least 40% of the total pore volume, as determined by mercury porosimetry;

wherein the ratio $r_{pv}$ of the pore volume contained in pores with a diameter in the range of more than 1 to 10 $\mu m$ to the pore volume contained in pores with a diameter in the range of 0.1 to 1 $\mu m$ is at most 0.50.

In a preferred embodiment, the porous alpha-alumina support is in the form of individual shaped bodies, e.g., in a shape as described above. Preferably, the porous alpha-alumina catalyst support is in the form of individual shaped bodies having a circumferential surface, a first side surface, a second side surface and at least one internal passageway extending from the first side surface to the second side surface.

Preferably, the quotient of the geometric surface of the catalyst support $SA_{geo}$ over the geometric volume of the catalyst support $V_{geo}$ ($SA_{geo}/V_{geo}$) is at least 1.1 $mm^{-1}$ and at most 10 $mm^{-1}$. Preferably, the quotient of $SA_{geo}$ over $V_{geo}$ is in the range of 1.15 $mm^{-1}$ to 5.0 $mm^{-1}$, more preferably in the range of 1.2 $mm^{-1}$ to 2.0 $mm^{-1}$. The geometric surface area $SA_{geo}$ and the geometric volume $V_{geo}$ are derived from the external, macroscopic dimensions of the porous alpha-alumina catalyst support taking into account the cross-sectional area, the height and, where applicable, the number of internal passageways. In other words, the geometric volume $V_{geo}$ of the catalyst support is the volume of a solid structure having the same outer dimensions, minus the volume occupied by passageways. Likewise, the geometric surface area $SA_{geo}$ is made up of the circumferential surface, the first and second face side surface and, where applicable, the surface defining the passageways. The first and second face side surface, respectively, is the surface area enclosed by the circumferential line of the face side, minus the cross-sectional areas of the passageways. The surface defining the passageways is the surface area lining the passageways.

A quotient of $SA_{geo}$ over $V_{geo}$ in the preferred range makes it possible for a better contact of the reaction gases with the catalyst surface to be obtained, which favors the conversion of the reactants and limits the inner diffusion phenomena, with a resulting increase in reaction selectivity.

The porous alpha-alumina support preferably does not have wash-coat particles or a wash-coat layer on its surface, so as to fully maintain the porosity of the uncoated support.

The porous alpha-alumina catalyst support may comprise impurities, such as sodium, potassium, magnesium, calcium, silicon, iron and/or zirconium. Such impurities may be introduced by components of the precursor material, in particular certain inorganic bond materials. In one embodiment, the porous alpha-alumina catalyst support comprises a total amount of 10 to 1,500 ppmw of sodium and potassium;

10 to 2,000 ppmw of calcium;

10 to 1,000 ppmw of magnesium; and/or 10 to 10,000 ppmw of silicon;

relative to the total weight of the support.

A low content of sodium is preferred in order to prevent segregation of the supported metal and to prevent alteration of the supported component.

The invention further relates to a shaped catalyst body for producing ethylene oxide by gas-phase oxidation of ethylene, i.e. an epoxidation catalyst, comprising at least 15 wt.-% of silver, relative to the total weight of the shaped catalyst body, deposited on a porous alpha-alumina catalyst support as described above.

The shaped catalyst body typically comprises 15 to 70 wt.-% of silver, preferably 20 to 60 wt.-% of silver, more preferably 25 to 50 wt.-% or 30 to 50 wt.-% of silver, relative to the total weight of the shaped catalyst body. A silver content in this range allows for a favorable balance between turnover induced by each shaped catalyst body and cost-efficiency of preparing the shaped catalyst body.

Besides silver, the shaped catalyst body may comprise one or more promoting species. A promoting species denotes a component that provides an improvement in one or more of the catalytic properties of the catalyst when compared to a catalyst not containing said component. The promoting species can be any of those species known in the art that function to improve the catalytic properties of the silver catalyst. Examples of catalytic properties include operability (resistance to runaway), selectivity, activity, turnover and catalyst longevity.

The shaped catalyst body may comprise a promoting amount of a transition metal or a mixture of two or more transition metals. Suitable transition metals can include, for example, the elements from Groups IIIB (scandium group), IVB (titanium group), VB (vanadium group), VIB (chromium group), VIIB (manganese group), VIIIB (iron, cobalt, nickel groups), IB (copper group), and IIB (zinc group) of the Periodic Table of the Elements, as well as combinations thereof. More typically, the transition metal is an early transition metal, i.e., from Groups IIIB, IVB, VB or VIB, such as, for example, hafnium, yttrium, molybdenum, tungsten, rhenium, chromium, titanium, zirconium, vanadium, tantalum, niobium, or a combination thereof. In one embodiment, the transition metal promoter(s) is (are) present in a total amount from 150 ppm to 5,000 ppm, typically 225 ppm to 4,000 ppm, most typically from 300 ppm to 3,000 ppm, expressed in terms of metal(s) relative to the total weight of the shaped catalyst body.

Of the transition metal promoters listed, rhenium (Re) is a particularly efficacious promoter for ethylene epoxidation high selectivity catalysts. The rhenium component in the shaped catalyst body can be in any suitable form, but is more typically one or more rhenium-containing compounds (e.g., a rhenium oxide) or complexes.

In some embodiments, the shaped catalyst body may include a promoting amount of an alkali metal or a mixture of two or more alkali metals. Suitable alkali metal promoters include, for example, lithium, sodium, potassium, rubidium, cesium or combinations thereof. The amount of alkali metal, e.g. potassium, will typically range from 50 ppm to 5,000 ppm, more typically from 300 ppm to 2,500 ppm, most typically from 500 ppm to 1,500 ppm expressed in terms of the alkali metal relative to the total weight of the shaped catalyst body. The amount of alkali metal is determined by the amount of alkali metal contributed by the porous alpha-alumina catalyst support and the amount of alkali metal contributed by the impregnation solution described below.

Combinations of heavy alkali metals like cesium (Cs) or rubidium (Rb) with light alkali metals like lithium (Li), sodium (Na) and potassium (K) are particularly preferred.

The shaped catalyst body may also include a Group IIA alkaline earth metal or a mixture of two or more Group IIA alkaline earth metals. Suitable alkaline earth metal promoters include, for example, beryllium, magnesium, calcium, strontium, and barium or combinations thereof. The amounts of alkaline earth metal promoters can be used in amounts similar to those used for the alkali or transition metal promoters.

The shaped catalyst body may also include a promoting amount of a main group element or a mixture of two or more main group elements. Suitable main group elements include any of the elements in Groups IIIA (boron group) to VIIA (halogen group) of the Periodic Table of the Elements. For example, the shaped catalyst body can include a promoting amount of sulfur, phosphorus, boron, halogen (e.g., fluorine), gallium, or a combination thereof.

The shaped catalyst body may also include a promoting amount of a rare earth metal or a mixture of two or more rare earth metals. The rare earth metals include any of the elements having an atomic number of 57-103. Some examples of these elements include lanthanum (La), cerium (Ce), and samarium (Sm). The amount of rare earth metal promoters can be used in amounts similar to those used for the transition metal promoters.

The invention further relates to a process for preparing a shaped catalyst body as described above, comprising a) impregnating a porous alpha-alumina catalyst support as described above with a silver impregnation solution, preferably under reduced pressure; and optionally subjecting the impregnated porous alumina support to drying; and b) subjecting the impregnated porous alpha-alumina support to a heat treatment;

wherein steps a) and b) are optionally repeated.

It is understood that all embodiments of the shaped catalyst body also apply to the process for preparing the shaped catalyst body, where applicable.

In order to obtain a shaped catalyst body having high silver contents, steps i) and ii) can be repeated several times. In that case it is understood that the intermediate product obtained after the first (or subsequent up to the last but one) impregnation/calcination cycle comprises a part of the total amount of target Ag and/or promoter concentrations. The intermediate product is then again impregnated with the silver impregnation solution and calcined to yield the target Ag and/or promoter concentrations.

Any silver impregnation solution suitable for impregnating a refractory support known in the art can be used. Silver impregnation solutions typically contain a silver carboxylate, such as silver oxalate, or a combination of a silver carboxylate and oxalic acid, in the presence of an aminic complexing agent like a $C_1$-$C_{10}$-alkylenediamine, in particular ethylenediamine. Suitable impregnation solutions are described in EP 0 716 884 A2, EP 1 115 486 A1, EP 1 613 428 A1, U.S. Pat. No. 4,731,350 A, WO 2004/094055 A2, WO 2009/029419 A1, WO 2015/095508 A1, U.S. Pat. Nos. 4,356,312 A, 5,187,140 A, 4,908,343 A, 5,504,053 A, WO 2014/105770 A1 and WO 2019/154863.

During heat treatment, liquid components of the silver impregnation solution evaporate, causing a silver compound comprising silver ions to precipitate from the solution and be deposited onto the porous support. At least part of the deposited silver ions is subsequently converted to metallic silver upon further heating. Preferably, at least 70 mol-% of the silver compounds, preferably at least 90 mol-%, more preferably at least 95 mol-% and most preferably at least 99.5 mol-% or at least 99.9 mol-%, i.e. essentially all of the silver ions, based on the total molar amount of silver in the impregnated porous alpha-alumina support, respectively. The amount of the silver ions converted to metallic silver can for example be determined via X-ray diffraction (XRD) patterns.

The heat treatment may also be referred to as a calcination process. Any calcination processes known in the art for this purpose can be used. Suitable examples of calcination processes are described in U.S. Pat. Nos. 5,504,052 A, 5,646,087 A, 7,553,795 A, 8,378,129 A, 8,546,297 A, US 2014/0187417 A1, EP 1 893 331 A1 or WO 2012/140614 A1. Heat treatment can be carried out in a pass-through mode or with at least partial recycling of the calcination gas.

Heat treatment is usually carried out in a furnace. The type of furnace is not especially limited. For example, stationary circulating air furnaces, revolving cylindrical furnaces or conveyor furnaces may be used. In one embodiment, heat treatment constitutes directing a heated gas stream over the impregnated bodies. The duration of the heat treatment is generally in the range of 5 min to 20 h, preferably 5 min to 30 min.

The temperature of the heat treatment is generally in the range of 200 to 800° C., preferably 210 to 650° C., more preferably 220 to 500° C., most preferably 220 to 350° C. Preferably, the heating rate in the temperature range of 40 to 200° C. is at least 20 K/min, more preferably at least 25 K/min, such as at least 30 K/min. A high heating rate may be achieved by directing a heated gas over the impregnated refractory support or the impregnated intermediate catalyst at a high gas flow.

A suitable flow rate for the first gas and/or the second gas may be in the range of, e.g., 1 to 1,000 Nm³/h, 10 to 1,000 Nm³/h, 15 to 500 Nm³/h or 20 to 300 Nm³/h per kg of impregnated bodies. In a continuous process, the term "kg of impregnated bodies" is understood to mean the amount of impregnated bodies (in kg/h) multiplied by the time (in hours) that the gas stream is directed over the impregnated bodies. It has been found that when the gas stream is directed over higher amounts of impregnated bodies, e.g., 15 to 150 kg of impregnated bodies, the flow rate may be chosen in the lower part of the above-described ranges, while achieving the desired effect.

Determining the temperature of the heated impregnated bodies directly may pose practical difficulties. Hence, when a heated gas is directed over the impregnated bodies during heat treatment, the temperature of the heated impregnated bodies is considered to be the temperature of the gas immediately after the gas has passed over the impregnated bodies. In a practical embodiment, the impregnated bodies are placed on a suitable surface, such as a wire mesh or perforated calcination belt, and the temperature of the gas is measured by one or more thermocouples positioned adjacent to the opposite side of the impregnated bodies which first comes into contact with the gas. The thermocouples are suitably placed close to the impregnated bodies, e.g., at a distance of 1 to 30 mm, such as 1 to 3 mm or 15 to 20 mm from the impregnated bodies.

The use of a plurality of thermocouples can improve the accuracy of the temperature measurement. Where several thermocouples are used, these may be evenly spaced across the area on which the impregnated bodies rest on the wire mesh, or the breadth of the perforated calcination belt. The average value is considered to be the temperature of the gas immediately after the gas has passed over the impregnated bodies. To heat the impregnated bodies to the temperatures as described above, the gas typically has a temperature of 220 to 800° C., more preferably 230 to 550° C., most preferably 240 to 350° C.

Preferably, heating takes place in a step-wise manner. In step-wise heating, the impregnated bodies are placed on a moving belt that moves through a furnace with multiple heating zones, e.g., 2 to 8 or 2 to 5 heating zones. Heat treatment is preferably performed in an inert atmosphere, such as nitrogen, helium, or mixtures thereof, in particular in nitrogen.

The invention further relates to a process for producing ethylene oxide by gas-phase oxidation of ethylene, comprising reacting ethylene and oxygen in the presence of a shaped catalyst body as described above.

It is understood that all embodiments of the shaped catalyst body also apply to the process for producing ethylene oxide in the presence of the shaped catalyst body, where applicable.

The epoxidation can be carried out by all processes known to those skilled in the art. It is possible to use all reactors which can be used in the ethylene oxide production processes of the prior art; for example externally cooled shell-and-tube reactors (cf. Ullmann's Encyclopedia of Industrial Chemistry, 5th edition, vol. A-10, pp. 117-135, 123-125, VCH-Verlagsgesellschaft, Weinheim 1987) or reactors having a loose catalyst bed and cooling tubes, for example the reactors described in DE 34 14 717 A1, EP 0 082 609 A1 and EP 0 339 748 A2.

The epoxidation is preferably carried out in at least one tube reactor, preferably in a shell-and-tube reactor. On a commercial scale, ethylene epoxidation is preferably carried out in a multi-tube reactor that contains several thousand tubes. The catalyst is filled into the tubes, which are placed in a shell that is filled with a coolant. In commercial applications, the internal tube diameter is typically in the range of 20 to 40 mm (see, e.g., U.S. Pat. No. 4,921,681 A) or more than 40 mm (see, e.g., WO 2006/102189 A1).

To prepare ethylene oxide from ethylene and oxygen, it is possible to carry out the reaction under conventional reaction conditions as described, for example, in DE 25 21 906 A, EP 0 014 457 A2, DE 23 00 512 A1, EP 0 172 565 A2, DE 24 54 972 A1, EP 0 357 293 A1, EP 0 266 015 A1, EP 0 085 237 A1, EP 0 082 609 A1 and EP 0 339 748 A2. Inert gases such as nitrogen or gases which are inert under the reaction conditions, e.g. steam, methane, and also optionally reaction moderators, for example halogenated hydrocarbons such as ethyl chloride, vinyl chloride or 1,2-dichloroethane can additionally be mixed into the reaction gas comprising ethylene and molecular oxygen.

The oxygen content of the reaction gas is advantageously in a range in which no explosive gas mixtures are present. A suitable composition of the reaction gas for preparing ethylene oxide can, for example, comprise an amount of ethylene in the range from 10 to 80% by volume, preferably from 20 to 60% by volume, more preferably from 25 to 50% by volume and particularly preferably in the range from 25 to 40% by volume, based on the total volume of the reaction gas. The oxygen content of the reaction gas is advantageously in the range of not more than 10% by volume, preferably not more than 9% by volume, more preferably not more than 8% by volume and very particularly preferably not more than 7.5% by volume, based on the total volume of the reaction gas.

The reaction gas preferably comprises a chlorine-comprising reaction moderator such as ethyl chloride, vinyl chloride or 1,2-dichloroethane in an amount of from 0 to 15 ppm by weight, preferably in an amount of from 0.1 to 8 ppm by weight, based on the total weight of the reaction gas. The remainder of the reaction gas generally comprises hydrocarbons such as methane and also inert gases such as nitrogen. In addition, other materials such as steam, carbon dioxide or noble gases can also be comprised in the reaction gas.

The concentration of carbon dioxide in the feed (i.e. the gas mixture fed to the reactor) typically depends on the catalyst selectivity and the efficiency of the carbon dioxide removal equipment. Carbon dioxide concentration in the feed is preferably at most 3 vol.-%, more preferably less than 2 vol.-%, most preferably less than 1 vol.-%, relative to the total volume of the feed. An example of carbon dioxide removal equipment is provided in U.S. Pat. No. 6,452,027 B1.

The above-described constituents of the reaction mixture may optionally each have small amounts of impurities. Ethylene can, for example, be used in any degree of purity suitable for the gas-phase oxidation according to the invention. Suitable degrees of purity include, but are not limited to, "polymer-grade" ethylene, which typically has a purity of at least 99%, and "chemical-grade" ethylene which typically has a purity of less than 95%. The impurities typically comprise, in particular, ethane, propane and/or propene.

The reaction or oxidation of ethylene to ethylene oxide is usually carried out at elevated catalyst temperatures. Preference is given to catalyst temperatures in the range of 150 to 350° C., more preferably 180 to 300° C., particularly preferably 190 to 280° C. and especially preferably 200 to 280° C. The present invention therefore also provides a process as described above in which the oxidation is carried out at a catalyst temperature in the range 180 to 300° C., preferably 200 to 280° C. Catalyst temperature can be determined by thermocouples located inside the catalyst bed. As used herein, the catalyst temperature or the temperature of the catalyst bed is deemed to be the weight average temperature of the catalyst particles.

The reaction according to the invention (oxidation) is preferably carried out at pressures in the range of 5 to 30 bar. All pressures herein are absolute pressures, unless noted otherwise. The oxidation is more preferably carried out at a pressure in the range of 5 to 25 bar, such as 10 bar to 24 bar and in particular 14 bar to 23 bar. The present invention therefore also provides a process as described above in which the oxidation is carried out at a pressure in the range of 14 bar to 23 bar.

It has been found that the physical characteristics of the shaped catalyst body, especially the BET surface area and the pore size distribution have a significant positive impact on the catalyst selectivity. This effect is especially distinguished when the catalyst is operated at very high work rates, i.e., high levels of olefin oxide production.

The process according to the invention is preferably carried out under conditions conducive to obtain a reaction mixture containing at least 2.3 vol.-% of ethylene oxide. In other words, the ethylene oxide outlet concentration (ethylene oxide concentration at the reactor outlet) is preferably at least 2.3 vol.-%. The ethylene oxide outlet concentration is more preferably in the range of 2.5 to 4.0 vol.-%, most preferably in the range of 2.7 to 3.5 vol.-%.

The oxidation is preferably carried out in a continuous process. If the reaction is carried out continuously, the GHSV (gas hourly space velocity) is, depending on the type of reactor chosen, for example on the size/cross-sectional area of the reactor, the shape and size of the catalyst, preferably in the range from 800 to 10,000/h, preferably in the range from 2,000 to 8,000/h, more preferably in the range from 2,500 to 6,000/h, most preferably in the range from 4,500 to 5,500/h, where the values indicated are based on the volume of the catalyst.

According to a further embodiment, the present invention is also directed to a process for preparing ethylene oxide (EO) by gas-phase oxidation of ethylene by means of oxygen as disclosed above, wherein the EO-space-time-yield measured is greater than 180 $kg_{EO}/(m^3_{cat}h)$, preferably to an EO-space-time-yield of greater than 200 $kg_{EO}/m^3_{cat}h)$, such as greater than 250 $kg_{EO}/(m^3_{cat}h)$, greater than 280 $kg_{EO}/(m^3_{cat}h)$, or greater than 300 $kg_{EO}/(m^3_{cat}h)$. Preferably the EO-space-time-yield measured is less than 500 $kg_{EO}/(m^3_{cat}h)$, more preferably the EO-space-time-yield is less than 350 $kg_{EO}/(m^3_{cat}h)$.

The preparation of ethylene oxide from ethylene and oxygen can advantageously be carried out in a recycle process. After each pass, the newly formed ethylene oxide and the by-products formed in the reaction are removed from the product gas stream. The remaining gas stream is supplemented with the required amounts of ethylene, oxygen and reaction moderators and reintroduced into the reactor. The separation of the ethylene oxide from the product gas stream and its work-up can be carried out by customary methods of the prior art (cf. Ullmann's Encyclopedia of Industrial Chemistry, 5th edition, vol. A-10, pp. 117-135, 123-125, VCH-Verlagsgesellschaft, Weinheim 1987).

The invention is described in more detail by the accompanying drawings and the subsequent examples.

METHOD 1: NITROGEN SORPTION

Figure 1:
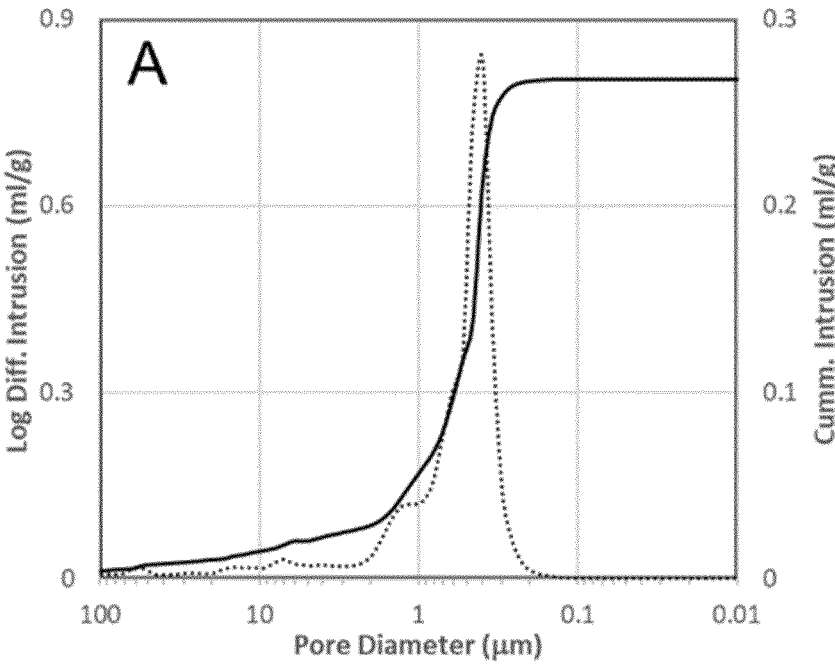
FIG. 1 shows the log differential intrusion [mL/g] and cumulative intrusion [mL/g] relative to the pore size diameter [mL/g] of inventive porous alpha-alumina catalyst support A, obtained by a process according to the invention.

Nitrogen sorption measurements were performed using a Micrometrics ASAP 2420.

Nitrogen porosity was determined in accordance with DIN 66134.

METHOD 2: MERCURY POROSIMETRY

Mercury porosimetry was performed using a Micrometrics AutoPore IV 9500 mercury porosimeter (140 degrees contact angle, 485 dynes/cm Hg surface tension, 60,000 psia max head pressure). Mercury porosity was determined in accordance with DIN 66133.

METHOD 3: LOOSE BULK DENSITY

The loose bulk density was determined by pouring the boehmitic-derived alumina into a graduated cylinder via a funnel, taking care not to move or vibrate the graduated cylinder. The volume and weight of the boehmitic-derived alumina were determined. The loose bulk density was determined by dividing the volume in milliliters by the weight in grams.

METHOD 4: BET SURFACE AREA

The BET surface area was determined in accordance with DIN ISO 9277.

METHOD 5: CRYSTAL ANALYSIS

X-ray diffraction data of boehmitic starting materials was obtained via Cu radiation and a conventional laboratory diffractometer. The data was analyzed using a software called DIANNA (diffraction analysis of nanopowders) as described in Yatsenko and Tsybulya, Zeitschrift für Kristallographie, 233 (2018), pp. 61-66. DIANNA software implements the Debye equation, which models a diffraction pattern based on scattering contributions from all atom pairs in a crystal. ICDD (International Centre for Diffraction Data) card 59608 was used as a rigid group in this modeling. That is, unit cell parameters and fractional coordinates for boehmite were used as reported in card 59608 without any refinement in this survey. Several model diffraction pattern for boehmite crystallites were calculated and compared with one of the experimental diffraction patterns.

Model crystallites were all rectangular prisms. The smallest prism was 20 unit cells long in the crystallographic x direction (5.6 nm), 1.5 unit cells thick in the crystallographic y direction (1.8 nm) and 20 unit cells wide in the crystallographic z direction (7.2 nm). This cell is 64 nm$^3$ in volume. Crystallites as large as 13,000 nm$^3$ were modeled. Ensembles of crystallite size models, refined within DIANNA to assess their number fraction and weight fraction of the overall population of boehmite crystallites, were employed.

The following tables show crystal size distributions for Pural TH 200, Pural TM 100 and Pural SB1, i.e. boehmitic starting materials, which are further described below. Aspect ratios are determined by dividing the largest crystal dimension, i.e. the largest a, b and c value by the smallest crystal dimension, i.e. the smallest a, b and c value.

| Crystal Size Distribution of Pural SB 1 | | | | | |
|---|---|---|---|---|---|
| Length (a-axis) [nm] | Thickness (b-axis) [nm] | Width (c-axis) [nm] | Aspect Ratio | Crystal Amount [wt. %] | Cumulative Crystal Amount [wt. %] |
| 5.6 | 4.7 | 7.2 | 1.53 | 2.5 | 2.5 |
| 8.5 | 4.7 | 7.2 | 1.81 | 3.8 | 6.3 |
| 5.6 | 3.5 | 7.2 | 2.06 | 2.4 | 8.7 |
| 8.5 | 4.7 | 10.9 | 2.32 | 3.9 | 12.5 |
| 8.5 | 3.5 | 7.2 | 2.43 | 2.5 | 15.1 |
| 8.5 | 3.5 | 10.9 | 3.11 | 3.5 | 18.6 |
| 5.6 | 2.3 | 7.2 | 3.13 | 4.1 | 22.7 |
| 11.3 | 3.5 | 7.2 | 3.23 | 3.8 | 26.4 |
| 11.3 | 3.5 | 10.9 | 3.23 | 5.5 | 32.0 |
| 8.5 | 2.3 | 7.2 | 3.70 | 4.4 | 36.3 |
| 5.6 | 1.6 | 7.2 | 4.50 | 4.5 | 40.8 |
| 8.5 | 2.3 | 10.9 | 4.74 | 4.5 | 45.3 |
| 17.1 | 3.5 | 7.2 | 4.89 | 6.7 | 52.1 |
| 17.1 | 3.5 | 10.9 | 4.89 | 9.4 | 61.4 |
| 11.3 | 2.3 | 7.2 | 4.91 | 4.8 | 66.2 |
| 8.5 | 1.6 | 7.2 | 5.31 | 4.9 | 71.1 |
| 11.3 | 1.6 | 7.2 | 7.06 | 5.3 | 76.4 |
| 11.3 | 1.6 | 10.9 | 7.06 | 5.2 | 81.6 |
| 14.2 | 1.6 | 7.2 | 8.88 | 5.6 | 87.2 |
| 14.2 | 1.6 | 10.9 | 8.88 | 0.0 | 87.2 |
| 17.1 | 1.6 | 7.2 | 10.69 | 6.1 | 93.2 |
| 17.1 | 1.6 | 10.9 | 10.69 | 6.8 | 100.0 |

Thus, 15.1 wt.-% of the crystals of Pural SB 1 exhibit an aspect ratio of 3.0 or lower. 15.1 wt.-% exhibit an aspect ratio of 2.5 or lower.

| Crystal Size Distribution of Pural TM 100 | | | | | |
|---|---|---|---|---|---|
| Length (a-axis) [nm] | Thickness (b-axis) [nm] | Width (c-axis) [nm] | Aspect Ratio | Crystal Amount [wt. %] | Cumulative Crystal Amount [wt. %] |
| 17.1 | 14.5 | 14.6 | 1.18 | 6.1 | 6.1 |
| 17.1 | 18.2 | 14.6 | 1.25 | 9.3 | 15.5 |
| 5.6 | 5.9 | 7.2 | 1.29 | 8.9 | 24.4 |
| 17.1 | 12 | 14.6 | 1.43 | 6.1 | 30.5 |
| 8.5 | 5.9 | 7.2 | 1.44 | 5.6 | 36.1 |
| 14.2 | 9.6 | 10.9 | 1.48 | 3.1 | 39.2 |
| 14.2 | 8.4 | 14.6 | 1.74 | 5.5 | 44.7 |
| 11.3 | 5.9 | 7.2 | 1.92 | 4.3 | 49.0 |
| 14.2 | 8.4 | 7.2 | 1.97 | 2.7 | 51.7 |
| 14.2 | 7.1 | 7.2 | 2.00 | 1.6 | 53.3 |
| 14.2 | 7.1 | 10.9 | 2.00 | 0.0 | 53.3 |
| 17.1 | 12 | 7.2 | 2.38 | 3.5 | 56.8 |
| 17.1 | 7.1 | 7.2 | 2.41 | 0.0 | 56.8 |
| 17.1 | 7.1 | 10.9 | 2.41 | 0.0 | 56.8 |
| 17.1 | 7.1 | 14.6 | 2.41 | 4.5 | 61.3 |
| 17.1 | 5.9 | 7.2 | 2.90 | 1.5 | 62.8 |
| 17.1 | 5.9 | 10.9 | 2.90 | 1.2 | 64.0 |
| 17.1 | 5.9 | 14.6 | 2.90 | 3.6 | 67.6 |
| 14.2 | 3.5 | 7.2 | 4.06 | 9.6 | 77.2 |
| 14.2 | 3.5 | 10.9 | 4.06 | 2.7 | 79.9 |
| 17.1 | 3.5 | 7.2 | 4.89 | 4.7 | 84.6 |
| 17.1 | 3.5 | 10.9 | 4.89 | 0.0 | 84.6 |
| 14.2 | 2.2 | 7.2 | 6.45 | 6.9 | 91.5 |
| 14.2 | 2.2 | 10.9 | 6.45 | 0.0 | 91.5 |
| 17.1 | 2.2 | 7.2 | 7.77 | 6.5 | 98.1 |
| 17.1 | 2.2 | 10.9 | 7.77 | 1.9 | 100.0 |

Thus, 67.6 wt.-% of the crystals of Pural TM 100 exhibit an aspect ratio of 3.0 or lower. 61.3 wt.-% exhibit an aspect ratio of 2.5 or lower.

| Crystal Size Distribution of Pural TH 200 | | | | | |
|---|---|---|---|---|---|
| Length (a-axis) [nm] | Thickness (b-axis) [nm] | Width (c-axis) [nm] | Aspect Ratio | Crystal Amount [wt. %] | Cumulative Crystal Amount [wt. %] |
| 14.2 | 12 | 10.9 | 1.30 | 2.7 | 2.7 |
| 14.2 | 19.4 | 14.6 | 1.37 | 2.0 | 4.7 |
| 14.2 | 9.6 | 10.9 | 1.48 | 5.4 | 10.1 |
| 14.2 | 9.6 | 7.2 | 1.48 | 3.2 | 13.3 |
| 22.8 | 19.4 | 29.3 | 1.51 | 11.4 | 24.8 |
| 11.3 | 9.6 | 14.6 | 1.52 | 6.8 | 31.6 |
| 14.2 | 9.6 | 14.6 | 1.52 | 5.0 | 36.5 |
| 22.8 | 19.4 | 14.6 | 1.56 | 10.4 | 46.9 |
| 17.1 | 14.5 | 10.9 | 1.57 | 0.7 | 47.6 |
| 11.3 | 9.6 | 7.2 | 1.57 | 4.1 | 51.8 |
| 11.3 | 19.4 | 14.6 | 1.72 | 2.8 | 54.6 |
| 25.6 | 14.5 | 18.3 | 1.77 | 0.5 | 55.0 |
| 17.1 | 9.6 | 7.2 | 1.78 | 3.6 | 58.6 |
| 17.1 | 9.6 | 14.6 | 1.78 | 5.9 | 64.5 |
| 11.3 | 9.6 | 18.3 | 1.91 | 8.6 | 73.1 |
| 14.2 | 9.6 | 18.3 | 1.91 | 4.1 | 77.2 |
| 17.1 | 9.6 | 18.3 | 1.91 | 3.8 | 81.0 |
| 19.9 | 9.6 | 18.3 | 2.07 | 3.3 | 84.3 |
| 17.1 | 9.6 | 21.9 | 2.28 | 2.8 | 87.1 |
| 14.2 | 19.4 | 7.2 | 2.69 | 1.8 | 88.9 |
| 19.9 | 9.6 | 7.2 | 2.76 | 2.7 | 91.6 |
| 22.8 | 19.4 | 7.2 | 3.17 | 8.4 | 100.0 |

Thus, 91.6 wt.-% of the crystals of Pural TH 200 exhibit an aspect ratio of 3.0 or lower. 87.1 wt.-% exhibit an aspect ratio of 2.5 or lower.

Preparation of Porous Alpha-Alumina Catalyst Supports

The properties of the boehmitic-derived aluminas used to obtain porous alpha-alumina catalyst supports are shown in Table 1. The boehmitic-derived aluminas were obtained from Sasol.

TABLE 1

| | Bulk Density [g/L] | Pore Volume [mL/g] * | Median Pore Diameter [nm] * | Crystalline Phase | Amount of Block-Shaped Crystals of Boehmitic Starting Material [wt.-%] ** |
|---|---|---|---|---|---|
| Puralox TH 200/70 | 300 | 1.23 | 37.4 | delta | 91.6 [1] |
| Puralox TM 100/150 | 420 | 0.87 | 21.0 | gamma | 67.6[2] |
| Puralox SBa 200 | 650 | 0.5 | 10.0 | gamma | 15.1 [3] |

* determined by nitrogen sorption

** calculated by PXRD pattern analysis using DIANNA software; aspect ratio of at most 3.0

[1] the boehmitic starting material of Puralox TH 200/70 is believed to be a material available as Pural TH 200

[2] the boehmitic starting material of Puralox TM 100/150 is believed to be a material available as Pural TM 100

[3] the boehmitic starting material of Puralox SBa 200 is believed to be a material available as Pural SB1

Example 1—Preparation of Supports A, B and C

Boehmitic-derived aluminas and inorganic bond materials, as specified in Table 2, were mixed to obtain a powder mixture. Kollidon® VA64 (a vinylpyrrolidone-vinyl acetate copolymer from BASF) was added to the powder mixture. Water was then added to obtain a malleable precursor material. The amounts of all components are shown in Table 2.

The malleable precursor material was mixed to homogeneity via a mix-muller and subsequently extruded using a ram extruder to form shaped bodies. The shaped bodies were in the form of hollow cylinders having an outer diameter of about 10 mm and an inner diameter of about 5 mm. The extrudates were dried at 110° C. for approximately 16 h, followed by heat treatment in a muffle furnace at 600° C. for 2 h and subsequently at 1,500° C. for 2 h. Heat treatment was performed in an atmosphere of air.

TABLE 2

| Support | Boehmitic-Derived Alumina | Inorganic Bond Material | Burnout Material | Liquid |
|---|---|---|---|---|
| A | Puralox TH 200/70 340 g | Pural SB1 146 g | Kollidon VA64 15 g | Water 454 g |
| B | Puralox TM 100/150 340 g | Pural SB1 146 g | Kollidon VA64 15 g | Water 439 g |
| C * | Puralox SBa 200 340 g | Pural SB1 146 g | Kollidon VA64 15 g | Water 404 g |

* comparative example

Figure 2:
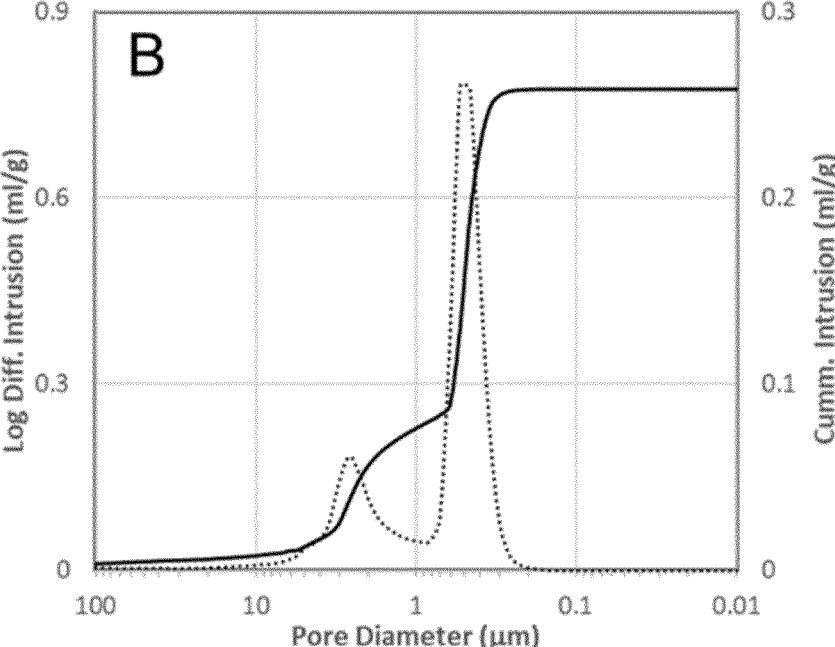
FIG. 2 shows the log differential intrusion [mL/g] and cumulative intrusion [mL/g] relative to the pore size diameter [mL/g] of inventive porous alpha-alumina catalyst support B, obtained by a process according to the invention.
Figure 3:
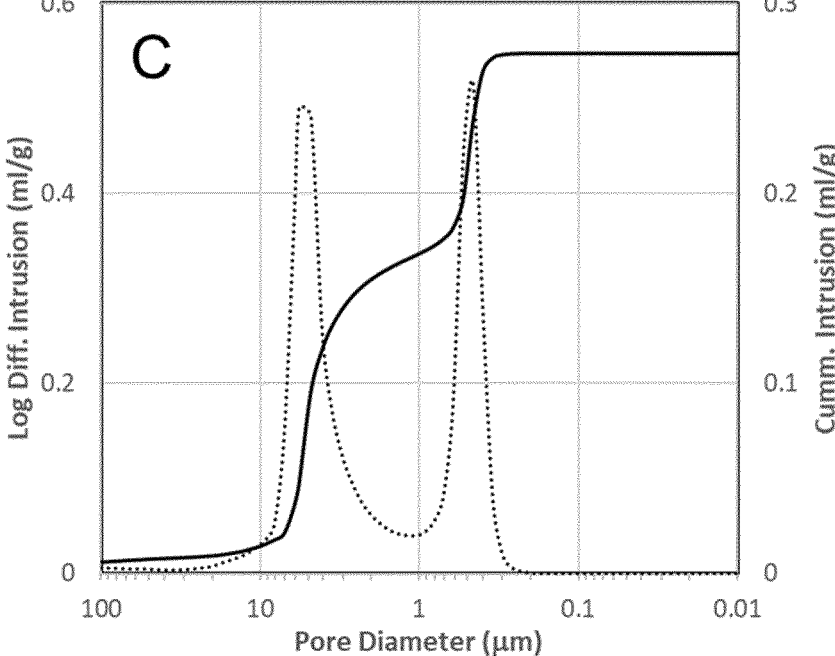
FIG. 3 shows the log differential intrusion [mL/g] and cumulative intrusion [mL/g] relative to the pore size diameter [mL/g] of comparative porous alpha-alumina catalyst support C.

Table 3 shows the physical properties of supports A, B, and C. FIGS. 1 to 3 show the log differential intrusion and cumulative intrusion relative to the pore size diameter of supports A, B, and C.

TABLE 3

| Support | BET Surface Area [m$^2$/g] | Pore Volume [mL/g] | Pore Volume Contained in Pores [mL/g] ** (Proportion of the Total Pore Volume) | | | | | $r_{pv}$ *** |
|---|---|---|---|---|---|---|---|---|
| | | | <0.1 μm | 0.1-1 μm | 1-10 μm | 10-100 μm | >100 μm | |
| A | 1.57 | 0.27 | 0 (0%) | 0.21 (77.9%) | 0.05 (16.9%) | 0.01 (5.2%) | 0 (0%) | 0.23 |
| B | 1.65 | 0.26 | 0 (0%) | 0.18 (71.0%) | 0.07 (25.9%) | 0.01% (3.1%) | 0 (0%) | 0.39 |
| C * | 1.03 | 0.27 | 0 (0%) | 0.11 (40.7%) | 0.15 (55.6%) | 0.01 (3.7%) | 0 (0%) | 1.44 |

* comparative example

** determined by mercury porosimetry

*** $r_{pv}$ = ratio of the pore volume contained in pores with a diameter in the range of more than 1 to 10 μm to the pore volume contained in pores with a diameter in the range of 0.1 to 1 μm It is evident that supports A, and B exhibit advantageously high proportions of pores with a diameter in the range of 0.1 to 1 μm in comparison to supports C. Supports A, and B also exhibit lower $r_{pv}$ values than supports C.

The surface area of supports A and B is significantly larger than that of support C.

The invention claimed is:

1. A process for producing a porous alpha-alumina catalyst support, comprising
    i) preparing a precursor material comprising a boehmitic-derived alumina having a pore volume of at least 0.6 mL/g as determined by nitrogen sorption, wherein the boehmitic-derived alumina is obtained by thermal decomposition of a boehmitic starting material and the boehmitic starting material predominantly comprises block-shaped crystals, and optionally an inorganic bond material;
    ii) forming the precursor material into shaped bodies; and
    iii) calcining the shaped bodies to obtain the porous alpha-alumina catalyst support.

2. The process according to claim 1, wherein the block-shaped crystals have an aspect ratio of at most 3.0, wherein the aspect ratio is defined as the ratio of the largest crystal dimension to the smallest crystal dimension.

3. The process according to claim 1, wherein the boehmitic starting material comprises at least 60 wt. % of block-shaped crystals, relative to the total weight of crystals constituting the boehmitic starting material.

4. The process according to claim 1, wherein the boehmitic starting material comprises boehmite and/or pseudo-boehmite.

5. The process according to claim 1, wherein the precursor material comprises, based on inorganic solids content, at least 50 wt. % wt. % of the boehmitic-derived alumina.

6. The process according to claim 1, wherein the boehmitic-derived alumina comprises alpha-alumina, a transition alumina, or a mixture thereof.

7. The process according to claim 6, wherein the transition alumina comprises at least 50 wt. % of a transition alumina having an average particle size of 10 to 100 μm, based on the total weight of transition alumina.

8. The process according to claim 1, wherein the boehmitic-derived alumina has a loose bulk density in the range of 50 to 600 g/L, a pore volume of 0.6 to 2.0 mL/g, as determined by nitrogen sorption, and a median pore diameter of at least 15 nm, as determined by nitrogen sorption.

9. The process according to claim 1, wherein the boehmitic-derived alumina has a total content of alkali metals of at most 1500 ppm.

10. The process according to claim 1, wherein the precursor material comprises, based on inorganic solids content, 1 to 30 wt.-% of the inorganic bond material.

11. The process according to claim 1, wherein the precursor material is formed into shaped bodies via extrusion, tableting, granulation casting, molding, or micro-extrusion.

12. The process according to claim 1, wherein calcining is performed at a temperature of at least 1300° C.

* * * * *